United States Patent [19]

Roshdy

[11] Patent Number: 5,655,657
[45] Date of Patent: Aug. 12, 1997

[54] PACKAGE FOR SPECIMEN RETRIEVAL BAG

[75] Inventor: Constance Roshdy, New Egypt, N.J.

[73] Assignee: Ethicon, Inc., Somerville, N.J.

[21] Appl. No.: 533,236

[22] Filed: Sep. 25, 1995

[51] Int. Cl.⁶ .................................................. B65D 83/10
[52] U.S. Cl. ........................ 206/363; 206/438; 206/63.3; 206/490
[58] Field of Search .................................. 206/363–366, 206/368, 369, 438–439, 63.3, 486, 488–490

[56] References Cited

U.S. PATENT DOCUMENTS

| | | | |
|---|---|---|---|
| 3,295,740 | 1/1967 | Hall | 206/486 |
| 3,381,809 | 5/1968 | Thorley | 206/486 |
| 4,884,681 | 12/1989 | Roshdy et al. | 206/63.3 |
| 5,226,535 | 7/1993 | Rosdhy et al. | 206/364 |
| 5,351,822 | 10/1994 | Sinn | 206/363 |
| 5,487,469 | 1/1996 | Roshdy et al. | 206/363 |

*Primary Examiner*—Jimmy G. Foster
*Assistant Examiner*—Nhan T. Lam
*Attorney, Agent, or Firm*—Emil Richard Skula

[57] ABSTRACT

A foldable package for an endoscopic specimen retrieval bag device. The package has a base panel having a pair of opposed major sides and a pair of opposed minor sides. The trapezoid shape connecting panel having a pair of opposed major sides and a pair of opposed angulated sides is foldably connected along the first major side to one major side of the base panel. A trapezoid shaped cannula retention panel having a pair of opposed major sides and a pair of opposed angulated sides is foldably connected along one major side to the second major side of the connecting panel and a regularly shaped upper panel has a first side along which the upper panel is foldably connected to the second major side of the retention panel. The upper panel has a pair of opposed angulated sides and an upper side. A triangularly-shaped retaining panel has a pair of angulated sides meeting at a top apex, first and second bottom sides opposite to the apex separated by a slot, and is foldably connected to the upper side of the upper panel along the first bottom side. A regularly shaped back support panel having a top side, a pair of opposed angulated sides, and first and second bottom sides separated by a slot is foldably connected along top side to the second bottom side of the bag retaining panel. An endoscopic surgical retrieval bag is retained in the package after it is folded and assembled.

5 Claims, 7 Drawing Sheets

PACKAGE FOR SPECIMEN RETRIEVAL BAG

TECHNICAL FIELD

The field of art to which this patent application pertains is packages, in particular packages for endoscopic surgical instruments.

BACKGROUND OF THE INVENTION

Endoscopic surgical techniques (defined herein to include laparoscopic, thoracoscopic and arthroscopic) are becoming widely accepted by the medical profession. The utilization of endoscopic surgical procedures has eliminated the need for radical incisions into the fascia and musculature of a patient in order to access a particular internal part of the patient's body. In a typical endoscopic procedure, trocars are typically inserted into the body to penetrate through to body cavities, such as the abdominal cavity. The trocars typically consist of two primary components, the first of which is an elongated piercing instrument, known as an obturator. The trocar assembly also contains a trocar cannula in which the trocar obturator is housed. The trocar cannula remains in the body cavity after the trocar obturator is removed and serves as a pathway to and from the body cavity.

Various types of endoscopic instruments may be inserted through the trocar cannula pathway, including endoscopes, stapling apparatuses, cutting and ligating apparatuses, specimen retrieval bags and the like. In many surgical procedures, it is frequently necessary to remove tissue from the body. Accordingly, various types of endoscopic tissue retrieval instruments have been It is essential that the mouth of the endoscopic specimen retrieval bag is open wide enough so that specimens can be easily entered into the bag. Without support the mouth of the device may deform or close making it difficult for specimens to be placed into the bag. The package is designed to hold the mouth of the bag open until the supporting belt takes a set. The package is designed to maintain the opening of the bag and ensuring that the opening does not become deformed until use. The folder is designed to hold the bag which has been forced open, shape the belt of the bag until it takes a set during sterilization and maintain its shape.

It is also important that endoscopic specimen retrieval devices be packaged in such a manner that the devices are protected during shipping, handling, and, of course, during sterilization procedures. A device which becomes displaced or shifted in its package during sterilization, shipping, handling, etc., will typically tend to retain a resulting distorted shape, may become damaged. The bag may unravel and become unusable for an endoscopic surgical procedure. In addition, it is important that the endoscopic device be easily removable from a package in an operating room without damaging the retrieval bag or cannula or compromising their sterility. In addition, since a packaged endoscopic device is typically placed into a plastic overwrap envelope prior to sterilization, it is critical that the plastic overwrap be protected from the cannula to prevent punctures and tears. Once the plastic overwrap is punctured or torn, the sterility of the endoscopic device is compromised and the device must typically be disposed of since it cannot be resterilized in a hospital environment.

What is needed in this art are packages for endoscopic tissue retrieval devices which are easy and economical to manufacture and which protect the devices during shipping, sterilization and handling and which further prevent the devices from shifting in the package.

SUMMARY OF THE INVENTION

It is an object of the present invention to provide a package for an endoscopic specimen bag device which protects the bag during sterilization, handling, shipping and storage, but which allows the device to be easily removed in an operating room.

It is a further object of the present invention to provide a package which maintains the endoscopic device in a substantially fixed position within the package.

It is yet another object of the present invention to provide a package for an endoscopic specimen retrieval bag device which minimizes the possibility of tears or punctures to a plastic outer wrap.

It is a further object of the present invention to provide such a package which is easy and economical to manufacture.

Accordingly, a foldable package for an endoscopic specimen retrieval bag device is disclosed. The package has a base panel having a pair of opposed major sides and a pair of opposed minor sides. A trapezoid shaped connecting panel having a pair of opposed major sides and a pair of opposed angulated sides is foldably connected along a first major side to one major side of the base panel. A trapezoid shaped cannula retention panel, said retention panel having a pair of opposed major sides and a pair of opposed angulated sides, is foldably connected along one major side to the second major side of the connecting panel. An irregularly shaped upper panel has a first side along which said panel is foldably connected to the second major side of the retention panel. The upper panel also has a pair of opposed angulated sides and an upper side. A triangularly-shaped retaining panel has a pair of angulated sides meeting at a top apex, and, first and second bottom sides opposite to the apex, said bottom sides separated by a slot, and is foldably connected to the upper side of the upper panel along the first bottom side. An irregularly shaped bag support panel having a top side, a pair of opposed angulated sides, and first and second bottom sides separated by a slot and is foldably connected along the top side to the second bottom side of the bag retaining panel. The cannula of an endoscopic surgical retrieval bag is retained in the package by having a first opening extending from the connecting panel to the retention panel, a second opening in the retention panel extending into the upper panel, a slit in the retention panel connecting the first opening with the second opening, opposed fold lines located on either side of the slit forming flaps, a third opening in the bag retaining panel; and, a slit in the bag retaining panel extending from the third opening to the apex.

Yet another aspect of the present invention is the combination of the package of claim 1 and an endoscopic specimen retrieval bag device. The device has a cannula having a proximal and a distal end, and, a flexible specimen bag mounted to the distal end of the cannula. The flexible bag has an open mouth, a closed bottom and means for closing the mouth of the bag.

Other features and advantages of the invention will become more apparent from the following description and accompanying drawings.

DESCRIPTION OF PREFERRED EMBODIMENTS

Figure 1:
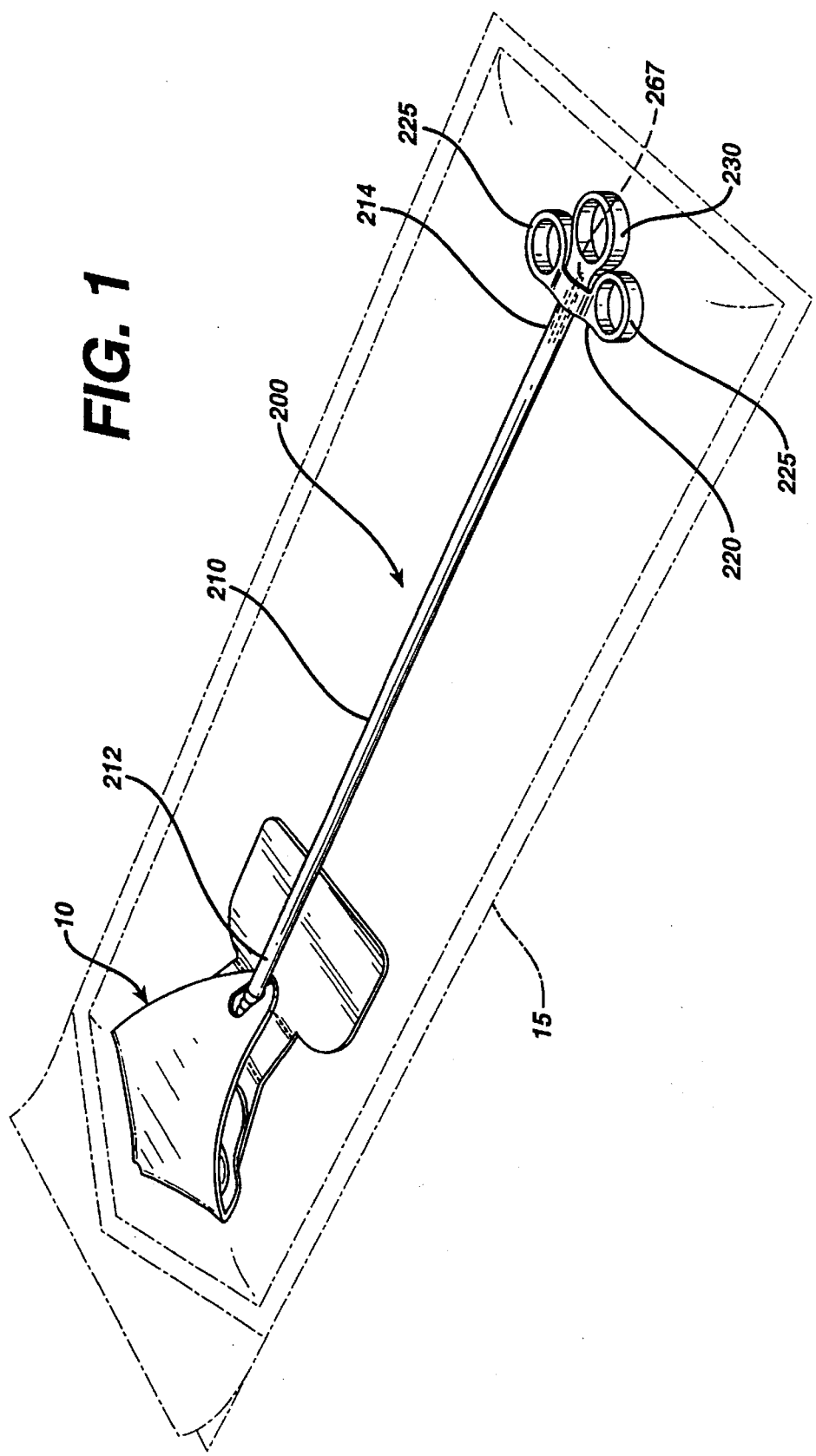
FIG. 1 is a perspective view of package of present invention containing an endoscopic specimen retrieval bag device contained within an outer blister package.

The package 10 of the present invention containing an endoscopic tissue retrieval pouch device 200 is seen in FIG. 1. The instrument 200 and package 10 are also seen to be contained in an outer blister package 15 as shown by phantom lines.

Figure 2:
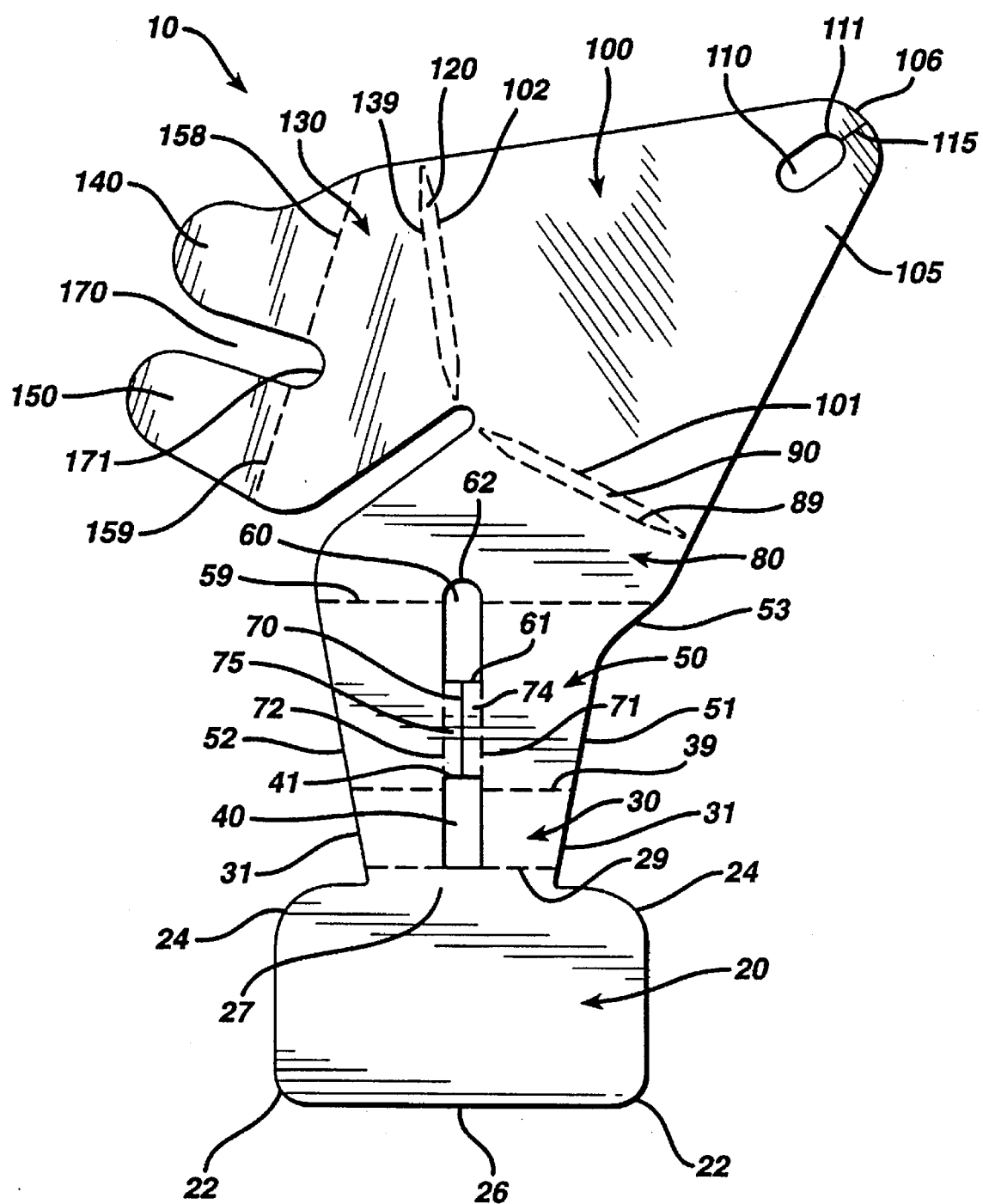
FIG. 2 is a plan view of a package of the present invention prior to assembly.
Figure 3:
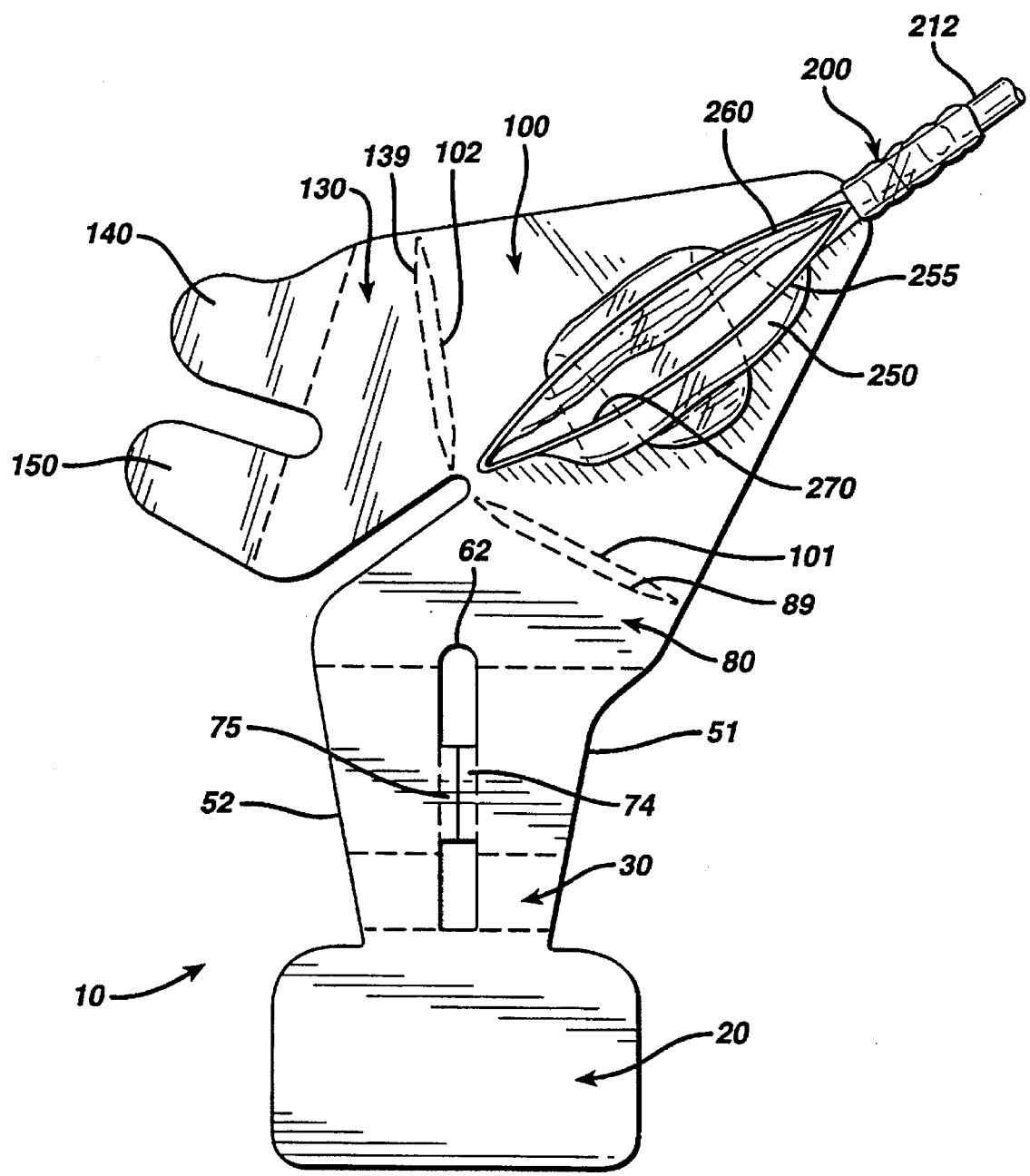
FIG. 3 illustrates the package of FIG. 2 wherein the bag section of the device is emplaced upon the baf retaining panel of the package.
Figure 4:
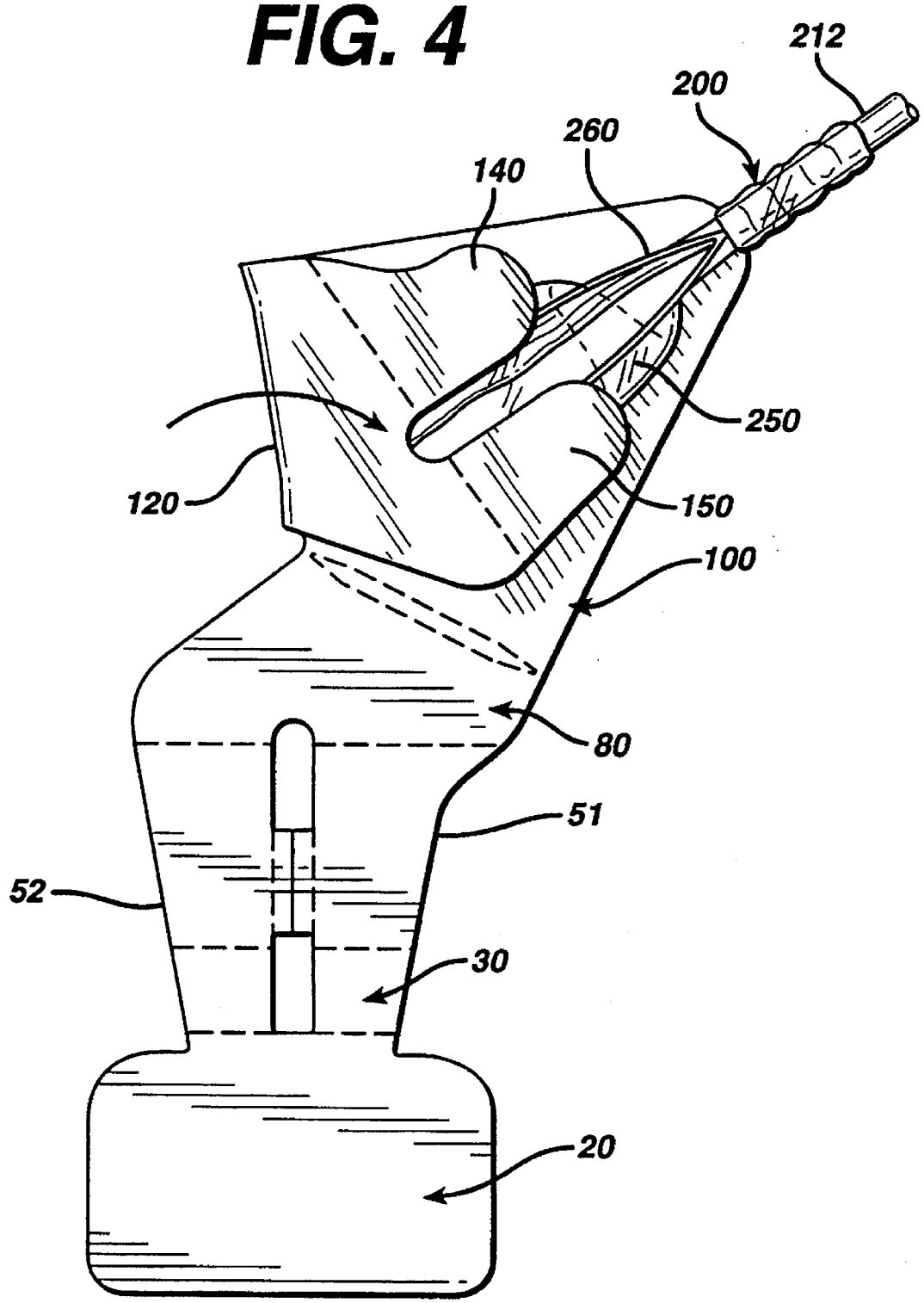
FIG. 4 is a top view of the package of the present invention partially assembled with the bag support panel folded onto the bag retaining panel.

Referring now to FIG. 2, the package 10 of the present invention is illustrated prior to folding and assembly, and is seen to have base panel 20. Base panel 20 is a substantially rectangular member having curved corners 22 and 24; if desired corners 22 and 24 may be angulated. Base panel 20 is seen to have first major side 26 and second opposed major side 27. The base panel 20 is connected along major side 27 to connecting panel 30 along fold line 29. Connecting panel 30 is seen to be a trapezoidal shaped panel having opposed angulated sides 31. The connecting panel 30 is seen to be foldably connected to the cannula retention panel 50 along fold line 39. The cannula retention panel 50 is seen to be a substantially trapezoidal shaped panel having opposed sides 51 and 52. The side 51 of panel 50 is seen to have upper outwardly extending section 53. The cannula retention panel 50 is foldably connected along fold line 59 to upper panel 80. Upper panel 80 is seen to be an irregularly shaped panel which is in turn connected to the bag retaining panel 100 along fold line 89. The gusset 90 is seen to be formed between the fold line 89 and the fold line 101. The cannula receiving opening 40 is seen to be contained in the connecting panel 30 and to extend partially into the cannula retaining panel 50. Opening 40 is substantially rectangularly shaped. The second cannula retaining opening 60 is seen to be contained in the panel 50, the rounded top 62 of the opening 60 is seen to extend into the upper panel 80. The bottom 61 of the second opening 60 is seen to be connected by the slit 70 to the top 41 of the first opening 40. The fold lines 72 and 71 are seen to be contained in panel 50 on either side of the slit 70 thereby forming the flaps 75 and 74.

The bag retaining panel 100 is connected along fold line 101 to the gusset 90. The panel 100 is a substantially triangularly shaped member having top section 105. The cannula receiving hole 110 is seen to be contained within the top section 105 of panel 100. The slit 115 is seen to extend from the top 111 of the opening 110 to the tip 106 of the top 105. The gusset 120 is seen to be formed by the fold line 102 and the fold line 139. Connected to the gusset 120 along fold line 139 is the irregularly shaped bag support panel 130. Connected to the bag support panel 130 along the fold lines 159 and 158 are the tongue panels 140 and 150. Tongue panels 140 and 150 are seen to be separated by slot 170. The rounded bottom 171 of slot 170 is seen to extend into panel 130.

A surgical retrieval pouch bag instrument 200 which can be packaged in the packages 10 of the present invention is seen in FIGS. 1, 3, 4, 5, 6 and 7. The instrument 200 is seen to have a cannula 210, having a distal end 212 and a proximal end 214. Mounted to the proximal end 214 is a handle 220 having fingerings 225. Extending from the distal end 212 of the shaft 210 is the flexible closure member 260. Mounted to the distal end of the shaft 210 is the specimen retrieval bag 250 having channel 255. The flexible closure member 260 is seen to be contained within the channel 255. The distal end 267 of the closure member 260 is seen to be connected to the thumb ring 230 adjacent to the proximal end 214 of the shaft 210. Proximal movement of the thumb ring and flexible closure member causes the opening 270 of the retrieval bag 250 to close.

A preferred technique for assembling the package 10 is illustrated in FIGS. 3–6. Initially, the bag is folded/collapsed and placed on bag support panel 100. Then the bag restraining panel 130 which also supports tongue panels 140 and 150 is rotated in a clockwise manner about fold lines 102 and 139 such that the top of panel 130 is resting on top of the folded bag. Next, panel 80 which also supports panels 20, 30, 51, and 52 is folded clockwise about fold lines 101 and 89 onto the top of panel 130. Next, bag collar restricting flaps 74 and 75 on panels 51 and 52 are pushed around the collar of the compressed belted bag and the cannula. Then cut out slot 110 with cut 115 is pushed around the cannula. The assembled package 10 containing the instrument 200 may then be inserted into a conventional plastic envelope 15 and the like.

Figure 7:
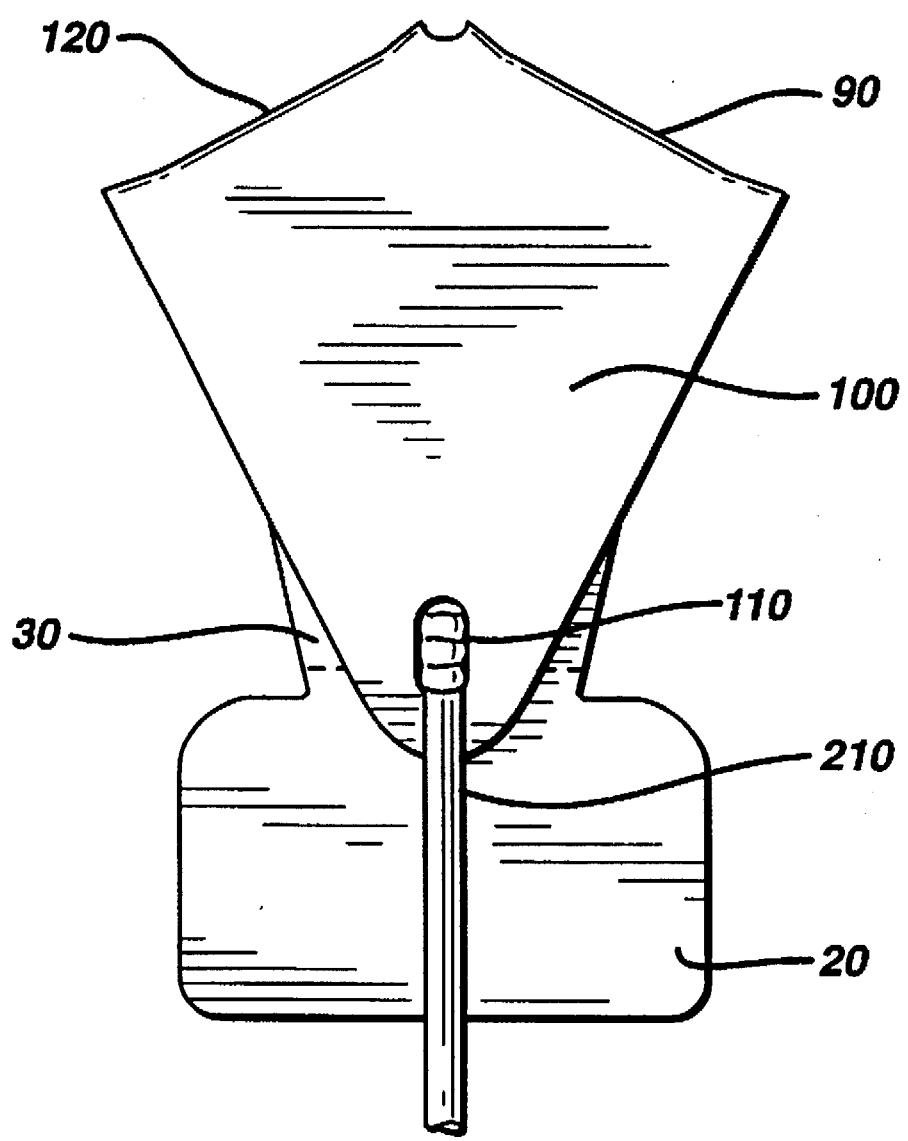
FIG. 7 illustrates the final step in the assembly of the package of the present invention wherein the end of the bag retaining panel is secured about the cannula of the surgical bag retrieval instrument.

The assembled package 10 containing the endoscopic specimen retrieval bag device 200 is seen in FIG. 7. The package 10 is shown inserted into a conventional plastic envelope 15 indicated by broken lines in FIG. 1.

Figure 5:
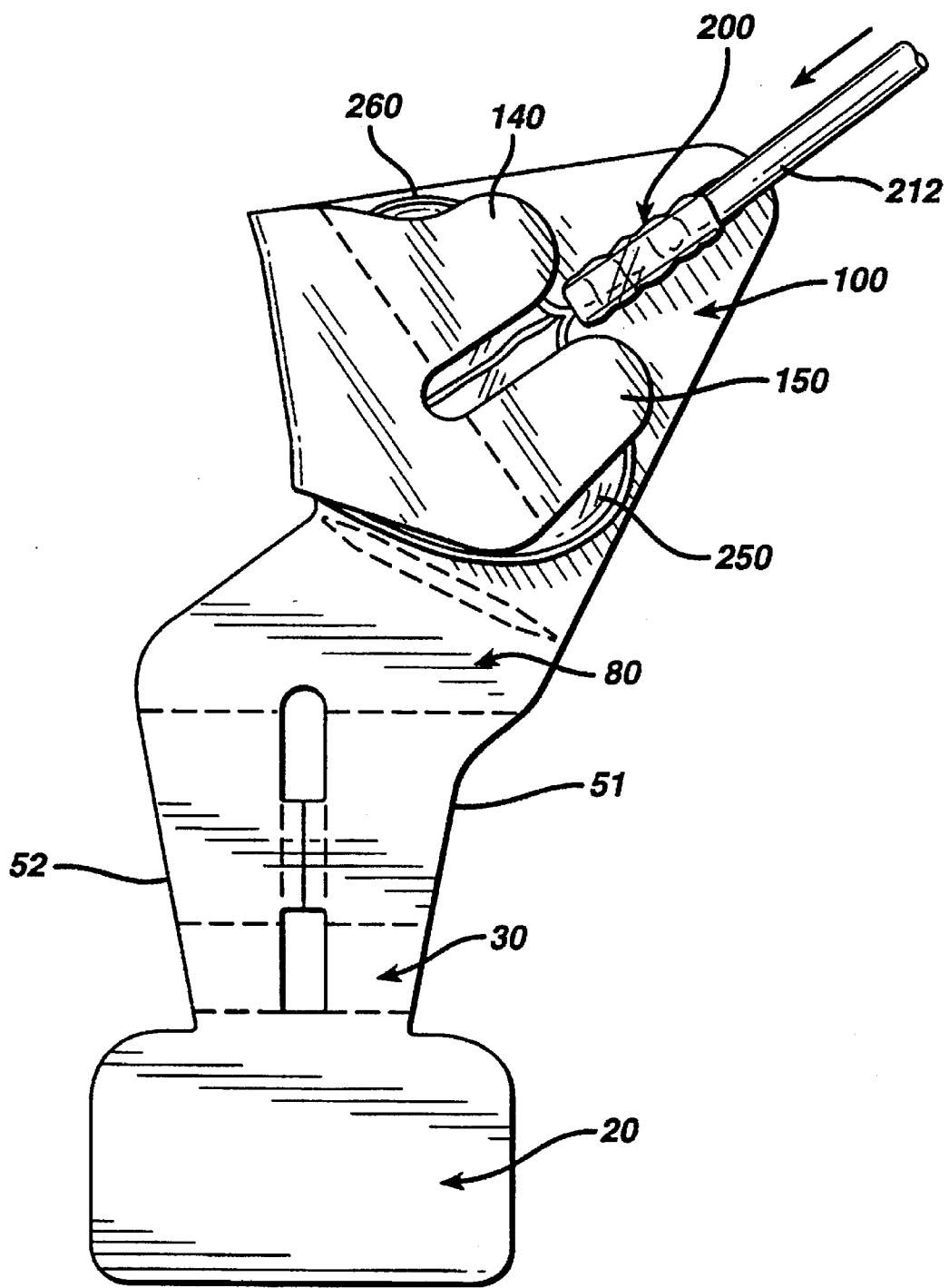
FIG. 5 is a top view of the package of the present invention partially assembled with the bag support panel and bag retaining panel folded onto the base panel, the upper panel, and the connecting panels.
Figure 6:
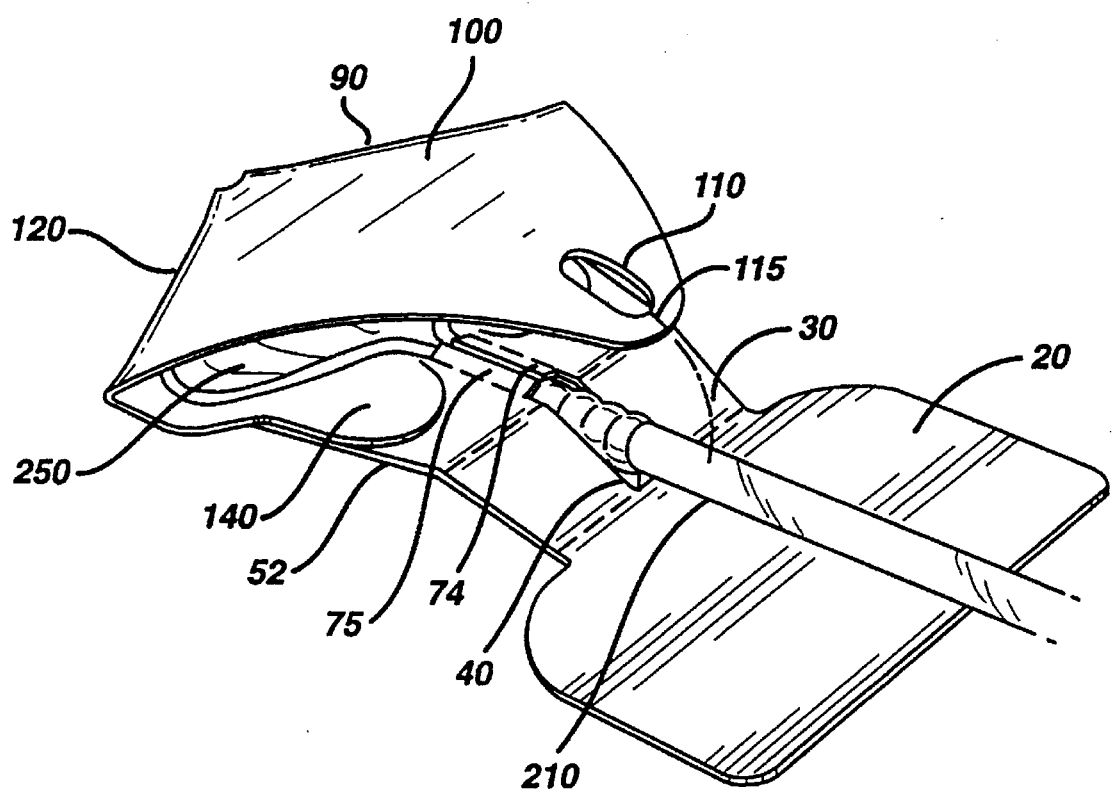
FIG. 6 illustrates the insertion of the distal end of an endoscopic retrieval bag device into the package of the present invention.

Referring to FIG. 1 and FIGS. 5 and 6, the package 10 is easily opened by pulling panel 20 away from the cannula of the bag device thereby releasing the bag collar/cannula from the restricting flaps 74 and 75 on panels 51 and 52. The folder than rotates about the cannula which is still contained in slot 110 with cut 115. After the folder rotates about the device, the cannula is released from slot 110 through cut 115.

The cannula of the device can be held in one hand and the other hand can remove the folder just by pulling panel 20.

The packages of the present invention may be constructed out of any material which is easily die cut and scored, and easily foldable, and which has sufficient strength and integrity to adequately protect the loop and catheter during sterilization, shipping, handling and storage. Such materials include conventional materials such as medical grade paperboard. It is particularly preferred to use a conventional, stiff paperboard having a thickness of about 0.008" to about 0.016". The paperboard, as previously mentioned, is preferably an appropriate medical grade. Other materials, including plastics, foils, and laminates combined with each other or with paper may also be used. The packages 10 are made using conventional equipment such as die cutting presses.

It will be appreciated by those skilled in the art that the size of the package 10 and the panels will vary in accordance with the size of the particular endoscopic device, e.g., endoscopic suturing device 200. The package 10 and the panels will be of sufficient size to effectively contain a particular endoscopic device such as device 200 illustrated and described herein. In addition the shapes and configurations of each panel may similarly vary.

The package 10 of the present invention containing the device 200 is typically further packaged by insertion into a conventional plastic envelope 15 or a conventional foil packet which is then sealed. Such a plastic envelope typically is made from conventional materials such as TYVEK®, paper polyfoil, polyester copolymer, polypropylene copolymer, combinations thereof, and the like.

The packaged medical devices are typically sterilized using conventional sterilization equipment and processes. Examples of the sterilization processes which can be used on the endoscopic specimen retrieval devices 200 packaged in the foldable package 10 of the present invention include conventional sterilization processes such as Co 60, irradiation, ethylene oxide, methylene bromide, and the like.

The one-piece package 10 of the present invention has many advantages. It is easy to manufacture out of conventional materials. The package 10 is extremely easy to assemble. An endoscopic device is retained and protected during sterilization, shipping, and handling. In particular, a suture is maintained in a fixed configuration. The package 10 is easily opened in an operating room environment, and the endoscopic specimen retrieval device can be easily removed from the package 10 in one continuous motion. The risk of damaging the device during removal from package 10 is substantially reduced. The package 10 additionally prevents a cannula from puncturing or tearing an outer plastic overwrap envelope.

Although this invention has been shown and described with respect to the detailed embodiments thereof, it will be understood by those skilled in the art that various changes and further detail thereof may be made without departing from the spirit and scope of the claimed invention.

What is claimed is:

1. A foldable package for an endoscopic specimen retrieval bag comprising a base panel having a pair of opposed major sides and a pair of opposed minor sides;

a trapezoid shaped connecting panel having a pair of opposed major sides and a pair of opposed angulated sides, said connecting panel foldably connected along a first major side to one major side of the base panel;

a trapezoid shaped cannula retention panel, said retention panel having a pair of opposed major sides and a pair of opposed angulated sides, said cannula retention panel foldably connected along one major side to the second major side of the connecting panel;

an irregularly shaped upper panel having a first side along which said upper panel is foldable connected to the second major side of the retention panel, said upper panel having a pair of opposed angulated sides and an upper side;

a triangularly-shaped retaining panel having a pair of angulated sides meeting at a top apex, and, first and second bottom sides opposite to the apex, said bottom sides separated by a slot, wherein the first bottom side is foldably connected to the upper side of the upper panel;

an irregularly shaped bag support panel having a top side, a pair of opposed angulated sides, and first and second bottom sides separated by a slot, the bag support panel is foldably connected along the top side to the second bottom side of the bag retaining panel; and, means for retaining a cannula of an endoscopic surgical retrieval bag.

2. The package of claim 1 wherein the means for retaining cannula comprise;

a first opening extending from the connecting panel to the retention panel;

a second opening in the retention panel extending into the upper panel;

a slit in the retention panel connecting the first opening with the second opening;

opposed fold lines located on either side of the slit forming flaps;

a third opening in the bag retaining panel; and, a slit in the bag retaining panel extending from the third opening to the apex.

3. The package of claim 1 further comprising a gusset between the upper side of the upper panel and the first bottom side of the bag retaining panel.

4. The package of claim 1 further comprising a gusset between the top side of the bag support panel and the second bottom side of the bag retention panel.

5. The combination comprising the package of claim 1 and an endoscopic specimen retrieval bag, said bag comprising a cannula having a proximal and a distal end, and, a flexible specimen bag mounted to the distal end of the cannula, said bag having an open mouth, a closed bottom and means for closing the mouth of the bag.

* * * * *